(12) United States Patent  
Ragsdale et al.

(10) Patent No.: US 7,799,555 B2
(45) Date of Patent: Sep. 21, 2010

(54) APPARATUS FOR HIGH-THROUGHPUT ELECTROPORATION

(75) Inventors: Charles W. Ragsdale, Concord, CA (US); John M. Fuller, Fairfield, CA (US); Nicholas R. Stephens, Crocket, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 879 days.

(21) Appl. No.: 11/627,235

(22) Filed: Jan. 25, 2007

(65) Prior Publication Data

US 2007/0249036 A1 Oct. 25, 2007

Related U.S. Application Data

(60) Provisional application No. 60/771,994, filed on Feb. 10, 2006.

(51) Int. Cl.
*C12M 1/42* (2006.01)

(52) U.S. Cl. .............. 435/285.2; 435/288.5; 435/305.3; 422/102; 324/450

(58) Field of Classification Search ............. 435/285.2, 435/288.4, 305.2, 305.3; 324/446, 448, 450
See application file for complete search history.

(56) References Cited

U.S. PATENT DOCUMENTS

| 4,230,983 | A | 10/1980 | Steere et al. |
| 4,801,546 | A | 1/1989 | Ackland |
| 5,218,312 | A | 6/1993 | Moro |
| 5,643,742 | A | 7/1997 | Malin et al. |
| 6,653,124 | B1 * | 11/2003 | Freeman ................ 435/297.1 |
| 6,686,193 | B2 | 2/2004 | Maher et al. |

FOREIGN PATENT DOCUMENTS

WO WO 2004/050866 A1 6/2004

* cited by examiner

*Primary Examiner*—William H Beisner
(74) *Attorney, Agent, or Firm*—Townsend and Townsend and Crew

(57) ABSTRACT

An electroporator for high-throughput electroporation is constructed with a well plate in which each well has internal electrodes that extend beyond the opening of the well to form contact areas, either as horizontal platforms extending laterally from the well rims or as extended heights of thin electrode plates. The electroporator also includes a lid that contains circuitry and electrical contacts that mate with the exposed contact areas in the well plate. The interchangeability of lids allows the wells to be shocked according to different protocols.

15 Claims, 9 Drawing Sheets

APPARATUS FOR HIGH-THROUGHPUT ELECTROPORATION

CROSS-REFERENCE TO RELATED APPLICATION

This application claims the benefit of U.S. Provisional Patent Application No. 60/771,994, filed Feb. 10, 2006, the contents of which are incorporated herein by reference in their entirety.

BACKGROUND OF THE INVENTION

1. Field of the Invention

This invention resides in the field of electroporation, a process for inserting exogenous molecular species into membranous structures by suspending the structures in a liquid solution of the exogenous species and applying an electric field to the suspension. In particular, this invention concerns apparatus used for high-throughput electroporation, which term is defined as electroporation performed in a multitude of cell suspensions either simultaneously or in rapid succession.

2. Description of the Prior Art

Electroporation is a technique that involves the use of an electric field to impregnate membranous structures such as living biological cells, liposomes, and vesicles with exogenous molecules. High-throughput electroporation allows a user to apply an electric field, i.e., to "shock," multiple samples either simultaneously or automatically in sequence. High-throughput electroporation is practiced in a variety of procedures, notably experiments involving siRNA and research involving the use of cDNA libraries.

A high-conductivity buffer is used as the medium in which the exogenous species are dissolved and the membranous structures suspended during electroporation, and normal saline is commonly used since, in addition to presenting a relatively low resistance to an electric current, it offers the most favorable environment for the viability of most cells. In general, however, electroporators are limited by their resistance to electrical energy. Hence, multi-welled plates, such as those with a standard 96-well array, are typically shocked in sections, such as one eight-well bank at a time until all twelve banks have been shocked.

One manufacturer, BTX Instrument Division, Harvard Apparatus, Inc., Holliston, Mass., USA, offers a high-throughput electroporator designed to shock the contents of 96 wells of an 8×12 array. This electroporator is described in an International Patent Application published under the Patent Cooperation Treaty, Publication No. WO 2004/050866 A1, the contents of which are incorporated herein by reference. The well plates described in WO 2004/050866 A1 are made with rectangular wells with electrodes plated on the walls of each well. All of the electrodes on one side of a bank of eight wells (i.e., a column) are connected in common to plated traces along each bank through wire connections, and all electrodes of the other side of the wells in the same bank are likewise connected in common. Corresponding electrical connections exist in all twelve banks. Because of the low resistance of eight parallel wells, however, and the fact that the maximum capacitor available has a capacitance of about 3200 mfd, the simultaneous shocking of eight wells limits the maximum time constant to about 20 msec and the resistance load to about 6.25 ohms. In many protocols, the shocking of all 96 wells requires ten minutes. The supply of electric power to the plate is achieved by lowering the plate into a plate handler which makes electrical contact between electric leads in the handler and each of the electrodes in the plate and has internal drivers or relays that connect each of the twelve banks in sequence to an external power supply. Electric pulses are then delivered to the electrodes in sequence. Rectangular wells of the same size and spacing are used for both 96-well plates and 25-well plates, and all electrical leads and connections are located in the "solid substrate" that forms the base of the plate. This limits the use of the wells and deprives the electroporator of versatility.

SUMMARY OF THE INVENTION

The present invention resides in electroporation plates that are an improvement over the prior art due to their ability to form electrical connections to a power supply by simple contact with electrical leads in a lid rather than in the plate itself or in a substrate supporting the plate. While the electrodes are in the interiors of the wells, either as linings on the walls of the wells or as plates or baffles immersed in the interior volumes of the wells, the connections with electrical leads in the lid are achieved by extensions of the electrodes to areas outside the wells. In certain embodiments, these extensions are lateral contact areas such as pads, shoulders, or platforms on the upper rim or edge or each well, while in other embodiments, these extensions are upper edges of the electrodes that protrude vertically above the wells. In all cases, the extensions are exposed for contact with opposing leads on the underside of the lid that are joined to a power source through electrical connections within the lid. In one group of embodiments, the electrodes in the well interiors are plated areas on opposing walls of the well, while in another group, the electrodes are baffles protruding from the well walls into the interior space of the well. Three or more baffles, although preferably four or five, are used in preferred embodiments, with alternating baffles connected to different polarities, i.e., odd numbered baffles connected for a negatively-charged polarity and even-numbered baffles for a positively-charged polarity. In a still further group of embodiments, the electrodes are thin plates spanning the entire width of the well. Three or more such plates are preferred, and most preferred are an even number such as four or more. In the case of thin plates with vertical upward extensions, the lid preferably contains individual contacts for each plate. When the electrodes are baffles whose lengths are less than the width of the well or thin plates spanning the width of the well are used, adjacent electrodes are closely spaced to provide only a narrow gap and hence a high voltage gradient between opposing electrodes without increasing the overall voltage to the plate. In certain embodiments as well, the electrodes, whether they be configured as wall linings, baffles, or thin plates, terminate a short distance above the floor of each well to accommodate adherent cells along the cell floor without direct contact between the cells and the electrodes.

The separation of the electrodes in the wells from the electric leads from the power supply by placing the former in the plate and the latter in the lid imparts versatility to the electroporator in a number of ways. For a given plate, a selection of lids can be used, each lid offering a different protocol for shocking the wells, or different lids shocking different numbers of wells, different groups of wells, or both. The circuitry in the lid can be configured to shock the wells in groups of which each group constitutes a fraction of the total number of wells in the plate, and shocking can occur in a predetermined sequence. The electroporator can also contain a computer or algorithm for shocking each group of wells individually according to a protocol that varies among the groups by waveform, voltage, capacitance, resistance, or combinations of these parameters, as well as other parameters such as pulse duration, amplitude, and frequency. For a given lid, a selection of plates can be used, each plate offering wells of different sizes, different arrangements or both, and different numbers and arrangements of exposed contact areas. The electroporator can also include a blank lid with no circuitry or electrical connections, for purposes of storage, transport, and operator handling.

These and other objects, features, and advantages are explained in more detail below.

DETAILED DESCRIPTION OF THE INVENTION AND PREFERRED EMBODIMENTS

Figure 1:
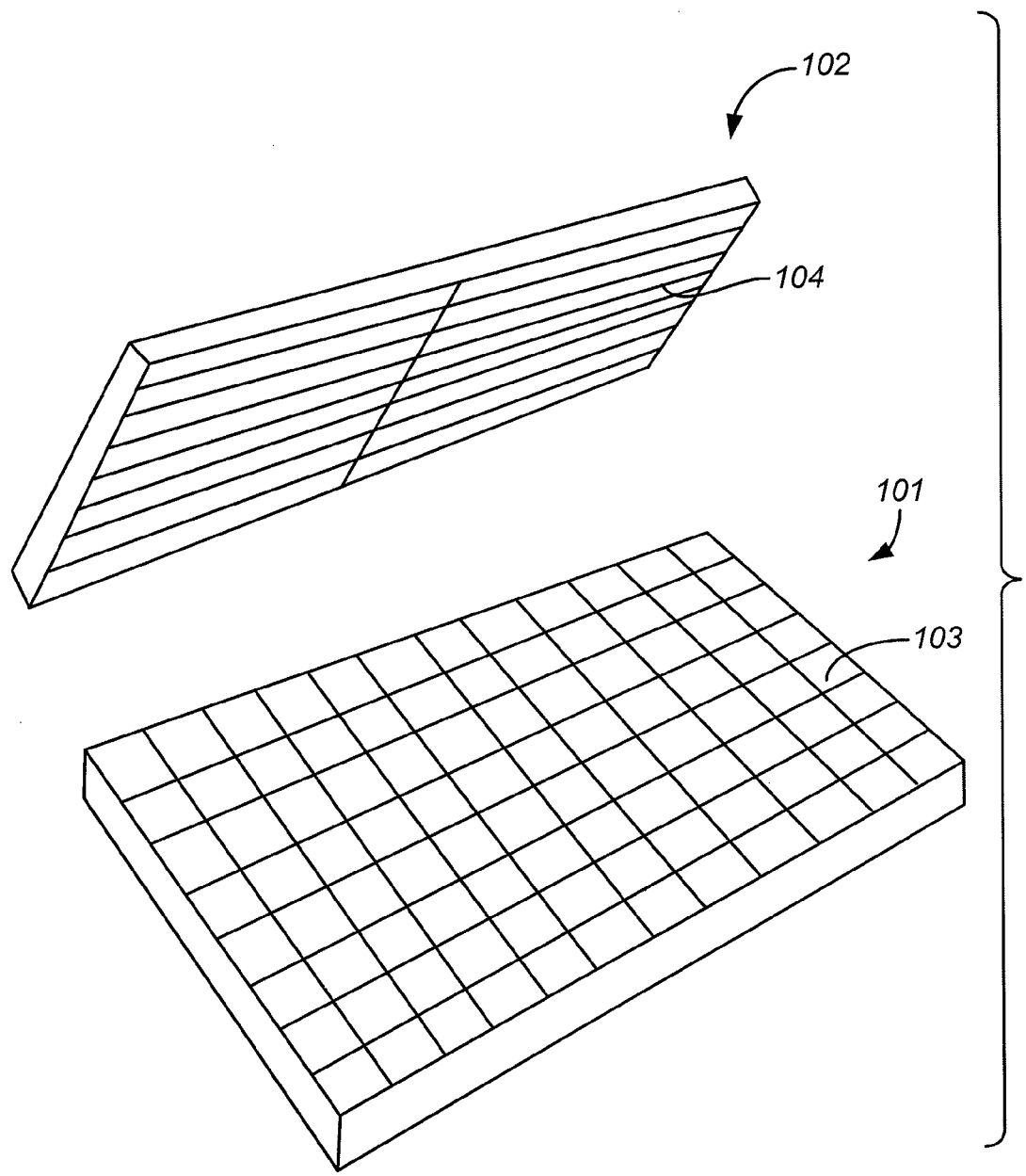
FIG. 1 is a perspective view of an electroporator in accordance with the present invention.

The term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein and an explicit teaching of this specification is intended to be resolved in favor of the teaching in this specification. This includes any discrepancy between an art-understood definition of a word or phrase and a definition explicitly provided in this specification of the same word or phrase.

While the features defining this invention are capable of implementation in a variety of constructions, the invention as a whole will be best understood by a detailed examination of specific embodiments. Several such embodiments are shown in the drawings.

FIG. 1 depicts the electroporation well plate 101 and lid 102 of an electroporator in accordance with the present invention. The plate 101 contains 96 wells 103 in a standard 12×8 array, and the lid 102 contains electric leads 104 that are exposed on its undersurface to make electrical contact with conductive contact areas on the supper surface of the plate.

Figure 2:
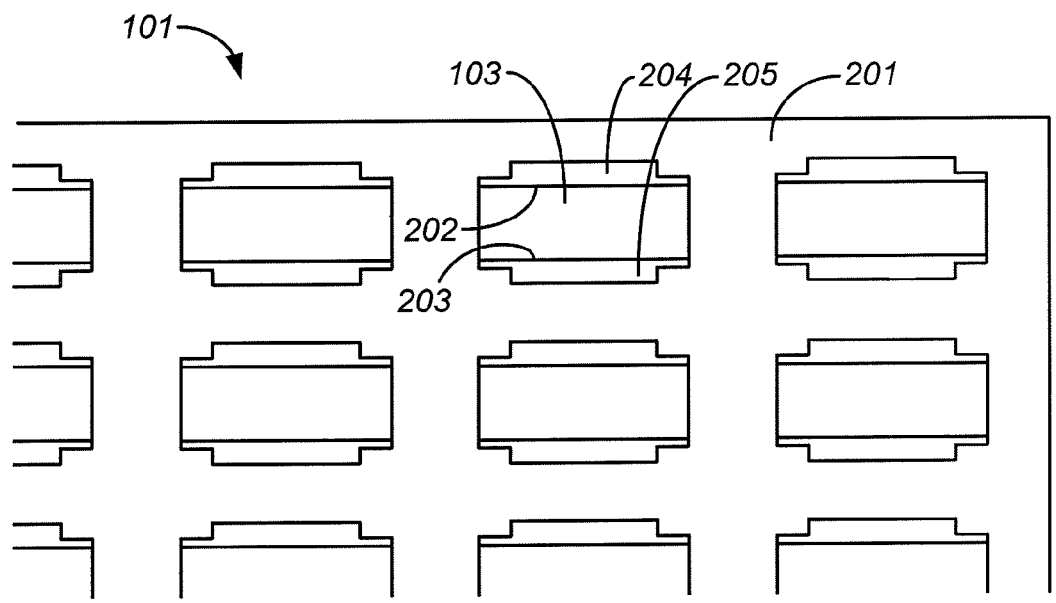
FIG. 2 is a top view of a portion of the well plate of the electroporator of FIG. 1.
Figure 3:
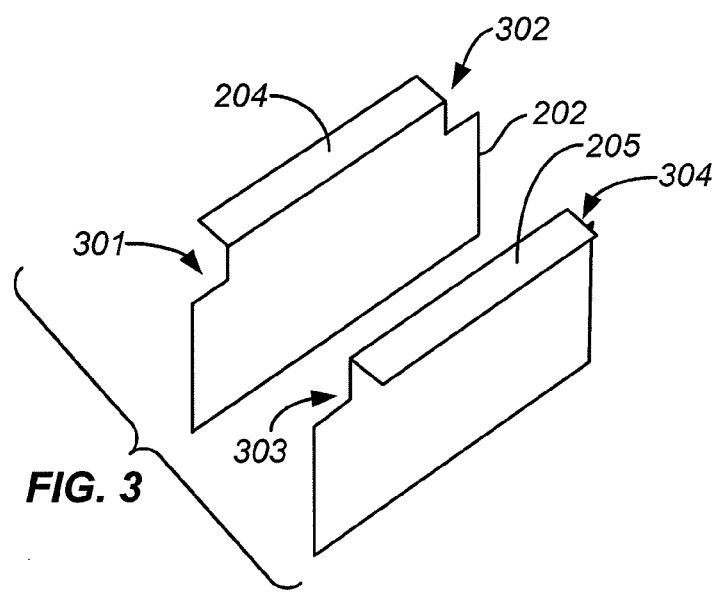
FIG. 3 is a perspective view of the electrodes from one well of the well plate of FIG. 2.

FIGS. 2 and 3 are respectively an enlarged view of a section of the upper surface 201 of the well plate 101 and a perspective view of the electrode pair 202, 203 of one well. The openings of the wells 103 are visible in FIG. 2. The wells are rectangular in shape, and each well has a pair of electrodes 202, 203 formed on opposing walls of the well by plating a conductive metal onto the wall surface. The plating extends past the upper edges of the walls to form lateral contact areas 204, 205 on the upper surface 201 of the plate. FIG. 3 shows that in addition to the contact areas 204, 205, each electrode has a notch, i.e., a corner cut-out, at each of its upper corners, the two electrodes together having four notches 301, 302, 303, 304. With these notches, the plated electrode areas are narrower in width at the tops of the wells than in the well interiors. These narrower widths at the tops provide a relatively wide spacing between the contact areas 204, 205 of adjacent wells and thereby prevent arcing between the wells.

Figure 4:
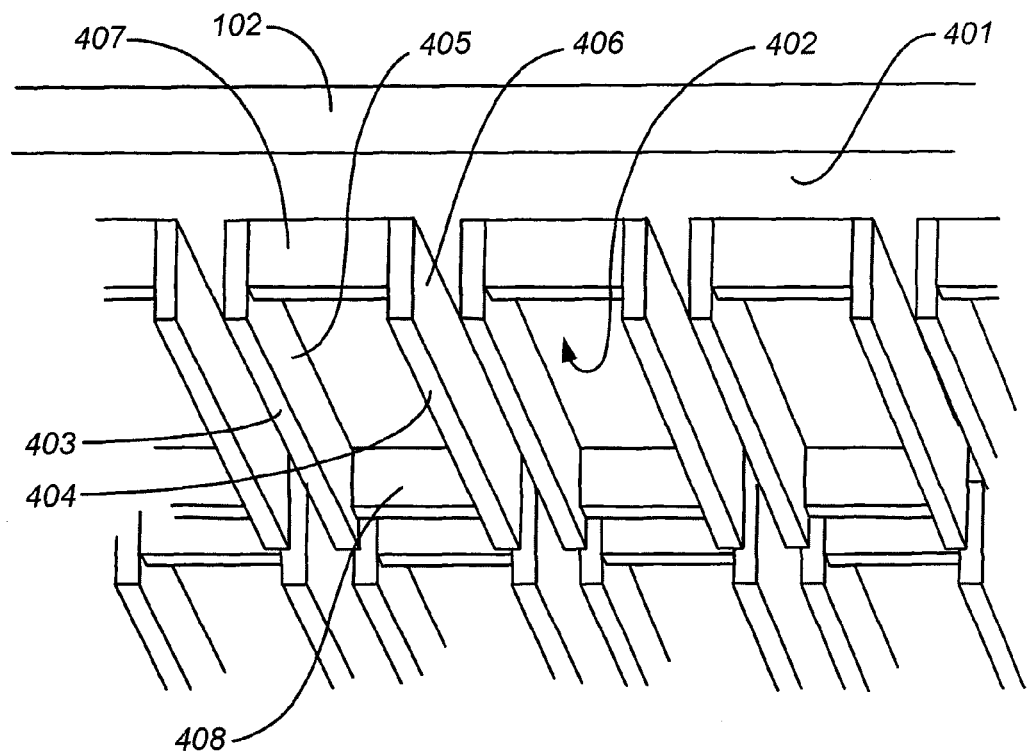
FIG. 4 is a perspective view of the underside of the lid of the electroporator of FIG. 1, showing a corner portion of the lid.

FIG. 4 is an enlarged view of the undersurface 401 of the lid 102. While the electric leads in the lid are not shown in FIG. 4, the undersurface of the lid is molded to form an array of inverted rectangular shells 402 opening downward, one shell to correspond to each of the wells in the well plate 101 (FIG. 1). The functional surfaces of each shell are the lower edges 403, 404 of the lateral walls 405, 406 of the shell. These lower edges 403, 404 are plated with conductive metal to which power is supplied by connective leads in the lid (not shown), and are positioned directly opposite to the contact areas 204, 205, respectively, of the electrodes on the well plate 101 (FIGS. 2 and 3). When the lid 102 is lowered over the well plate 101, electrical contact is made with the electrodes in each well, and the shells 402 cover the tops of the wells. For improved contact with the contact areas on the well plate, the plated edges 403, 404 of the shells 402 can optionally have a surface that is waffle-shaped, corrugated, or cross-hatched in contour. The end walls 407, 408 of each shell are of lesser vertical length than the lateral walls 405, 406 to leave a small opening along the upper rim at each end of each well. These openings allow the flow of gases into and out of the well during electroporation and thereby equalize any pressure differentials that might arise between any of the wells and their exteriors.

Figure 5:
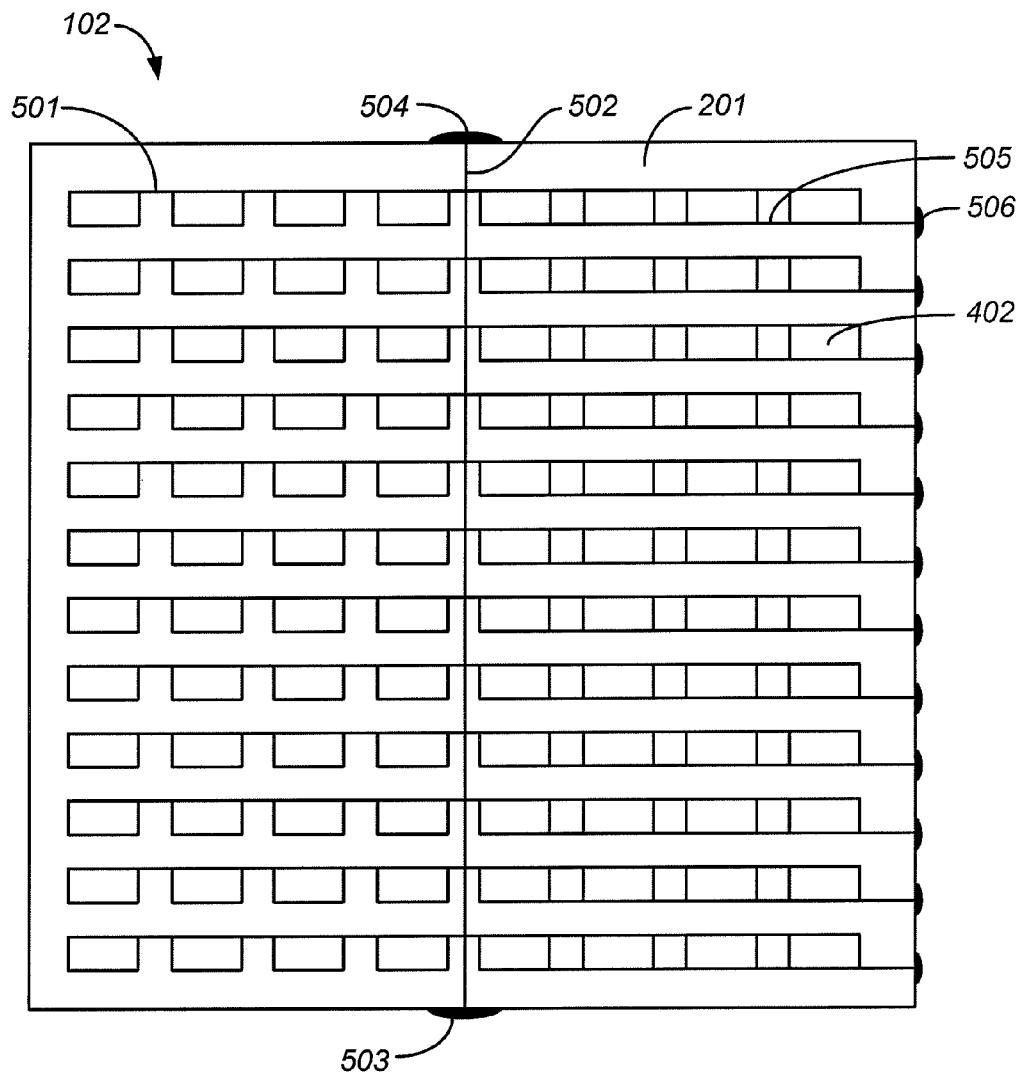
FIG. 5 is a plan view of the circuitry on the underside of the lid of the electroporator of FIG. 1, as viewed through the lid from the top.
Figure 6:
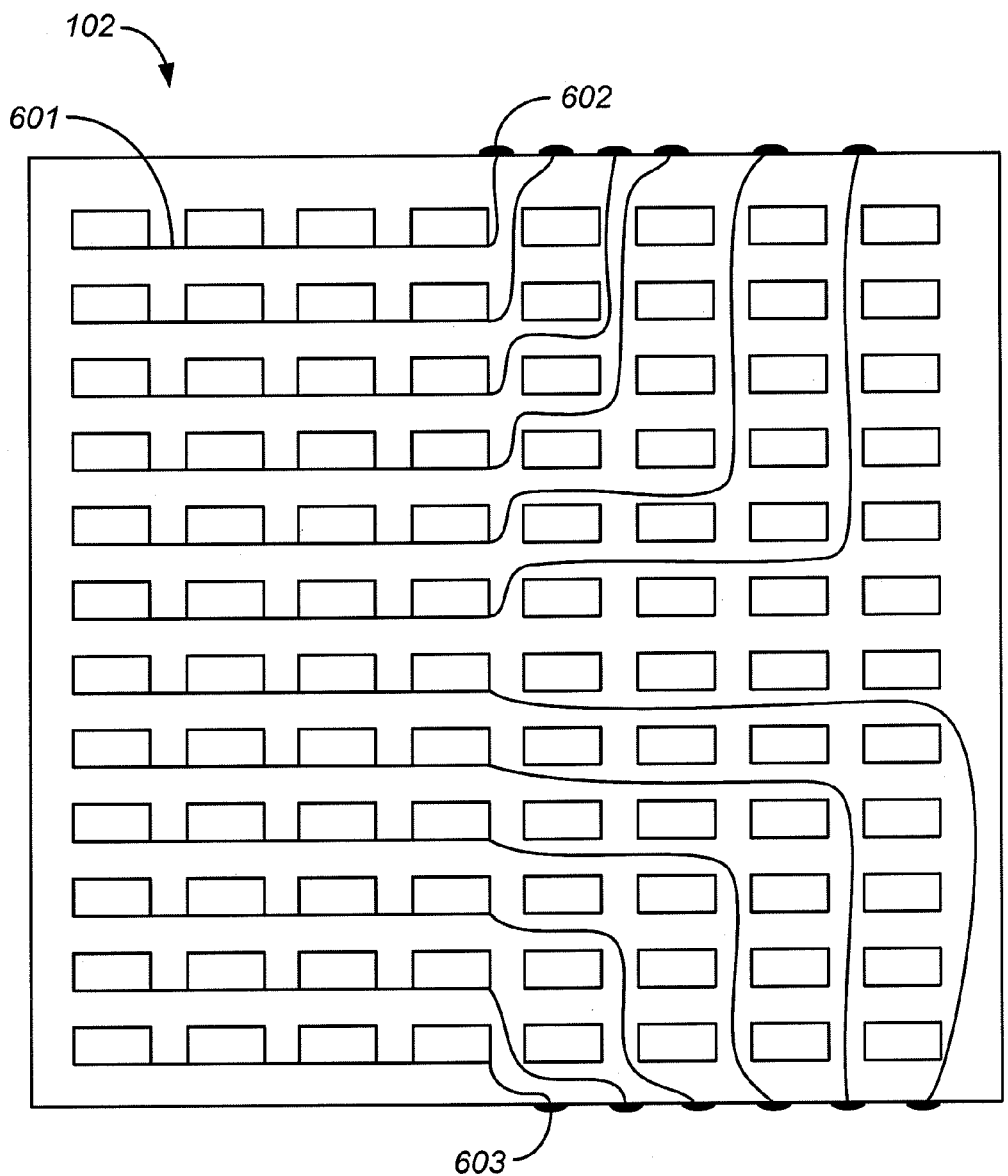
FIG. 6 is a plan view of the circuitry on the top side of the lid of the electroporator of FIG. 1, as viewed from the top.

In the embodiment shown in these Figures, the electric leads in the lid are distributed between the undersurface and the top surface of the lid. The arrangement of electric leads on the undersurface 201 is shown in FIG. 5 while the arrangement on the top surface is shown in FIG. 6. Both however are shown as they would be viewed through the top of the lid for ease of understanding how the power is distributed to all wells in the well array.

FIG. 5 shows that for each bank of eight wells, all electrodes on one side of the wells are connected to each other through lateral traces 501 and to a common trace 502 along the centerline of the plate. The two ends of the centerline trace 502 are joined to COM pads 503, 504 on the outside (front and rear, respectively) edges of the plate. For four wells in each eight-well bank, the electrodes on the other side are connected to each other through lateral traces 505 as well, and each of these is individually connected to contacts 506 along one side edge of the plate. The COM pads 503, 504 allow individual energization of each eight-well bank, while the individual contacts 506 allow individual energization of each of the four-well banks to which they are connected.

FIG. 6, representing the circuitry on the top side of the plate, shows the wiring for the remaining electrodes, i.e., the opposing electrodes in the leftmost four wells of each eight-well bank. Here, as in circuitry on the underside of the plate, each of the remaining leftmost four wells in a given bank are connected by traces 601, and each group of four is individually connected to contacts on the front and rear edges of the plate. The traces from the rearmost six banks terminate in contacts 602 on the rear edge while the traces from the front six banks terminate in contacts 603 on the front edge. While the contact areas on the lid that make contact with the plate are all on the undersurface of the lid, communication between those areas and the traces on the top of the lid can be made by plated-through holes or their equivalent, to reduce interference between different groups of traces. The arrangements shown in FIGS. 5 and 6 permit shocking of individual groups of four wells each in sequences that can be programmed by an external controller.

Figure 7:
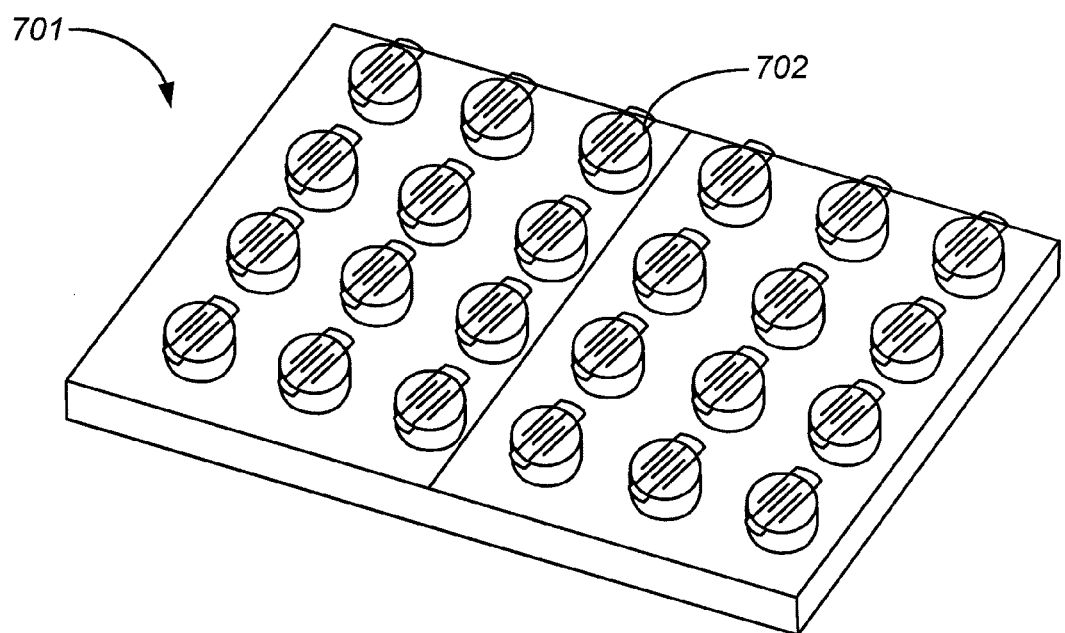
FIG. 7 is a perspective view of a well plate for an alternative electroporator of the present invention.
Figure 8:
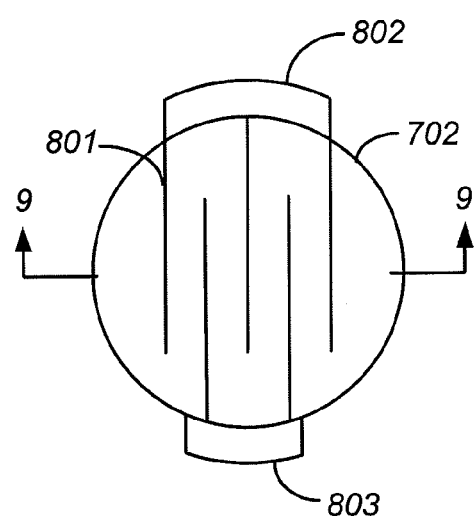
FIG. 8 is a top view of one well of the well plate of FIG. 7.
Figure 9:
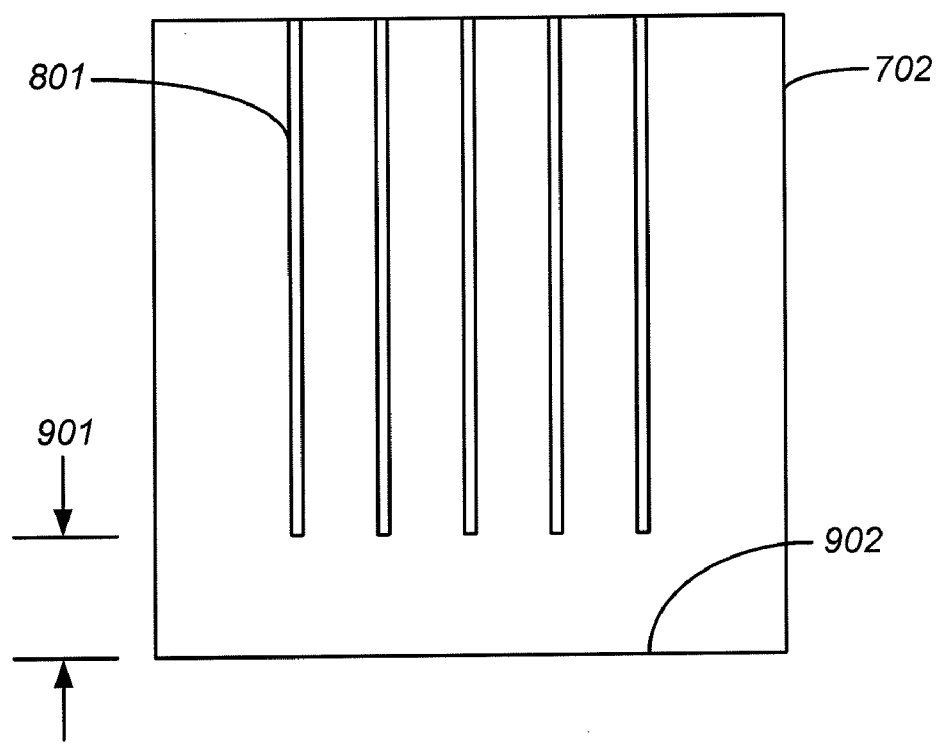
FIG. 9 is a cross section of the well of FIG. 8, taken along the line 9-9 thereof.

An alternative embodiment of an electroporator well plate for use in the practice of the invention is shown in FIGS. 7, 8, and 9. The well plate 701 of FIG. 7 contains 24 wells 702, which are shown as cylinders protruding upward from the upper surface of the plate, but can alternatively be indentations in the plate extending below its surface. The wells are shown as circular cylinders but can be square or rectangular, or other shapes. FIG. 8 is a top view of one well 702 and shows that the well contains a series of baffles 801 that are parallel but spaced apart sufficiently to allow the cells or other membranous structures suspended in the well to pass freely in the spaces between the vanes. The baffles 801 serve as electrodes and each baffle is plated on both sides with an electrically conductive metal. The baffles are electrically connected to conductive tabs 802, 803 extending laterally outward from the upper rim of each well, each tab forming a horizontal platform to serve as a contact area for electrical contacts in the lid. The baffles are connected in alternating manner to the tabs 802, 803, i.e., with odd-numbered baffles connected to one tab and even-numbered baffles to the other, to permit the baffles to be energized with charges of alternating polarity from one baffle to the next. While the embodiment shown in these Figures contains five baffles per well, the number of baffles can vary up to as large a number as the well can accommodate. In preferred structures, space is provided at the edges to allow insertion of a pipette tip. Alternatively, the center baffle can be designed to include a hollow vertical rib for insertion of a pipette tip. The cross section view of FIG. 9 shows that the baffles 801 in this particular embodiment terminate at their lower extremities a short distance 901 above the floor 902 of the well. This distance provides clearance for cells (or membranous structures in general), including adherent cells, at the bottom of the well while keeping the cells out of contact with the baffles. A typical contemplated distance 901 is 1-2 mm but can be greater, and the optimal distance can be determined by experimentation.

While the lid for the well plate represented by FIGS. 7, 8, and 9 is not shown, a lid analogous to the lid 102 of FIGS. 1 and 4 can be designed, with corresponding contact areas to match the contact areas 802, 803 of the well plate.

Figure 10:
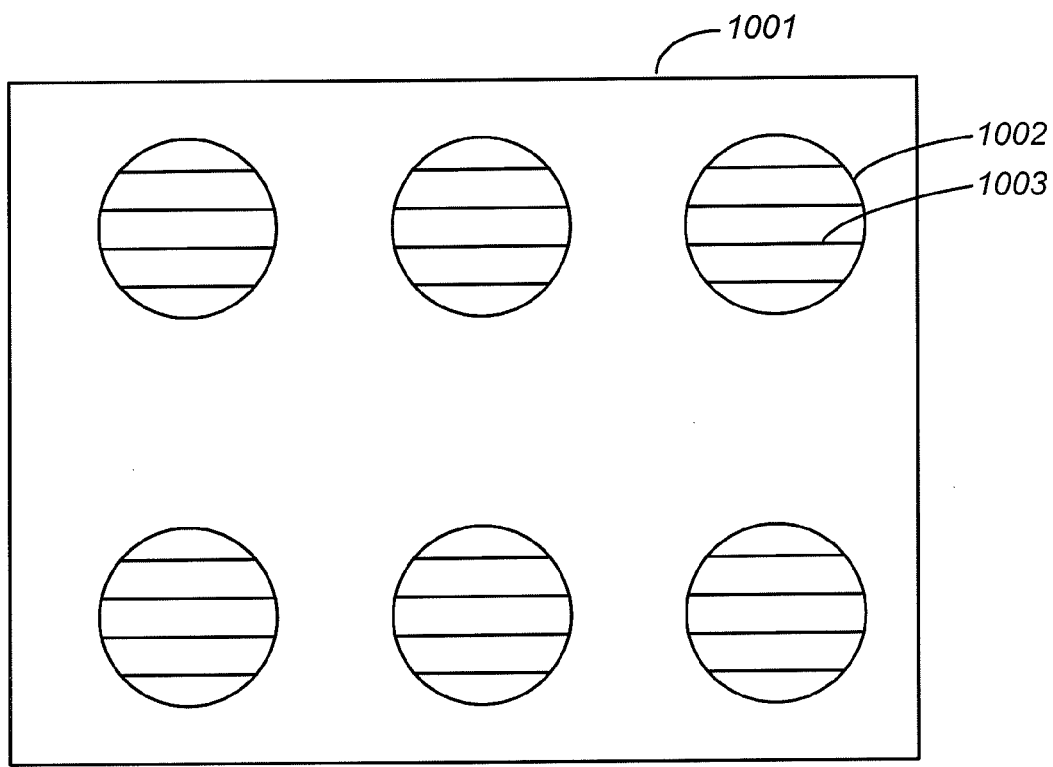
FIG. 10 is a top view of the well plate of a third electroporator of the present invention.
Figure 11:
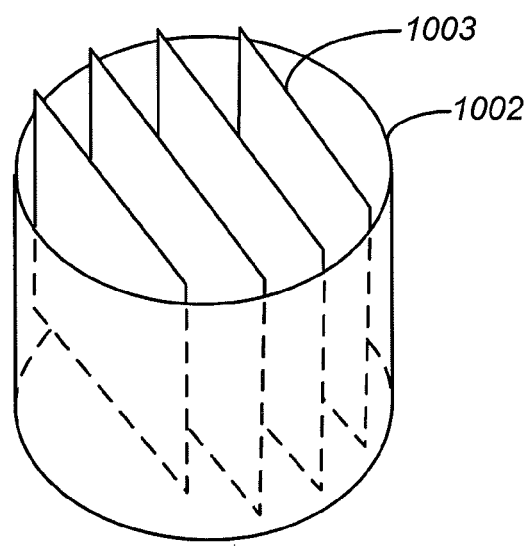
FIG. 11 is a perspective view of one well of the well plat of FIG. 10.
Figure 12:
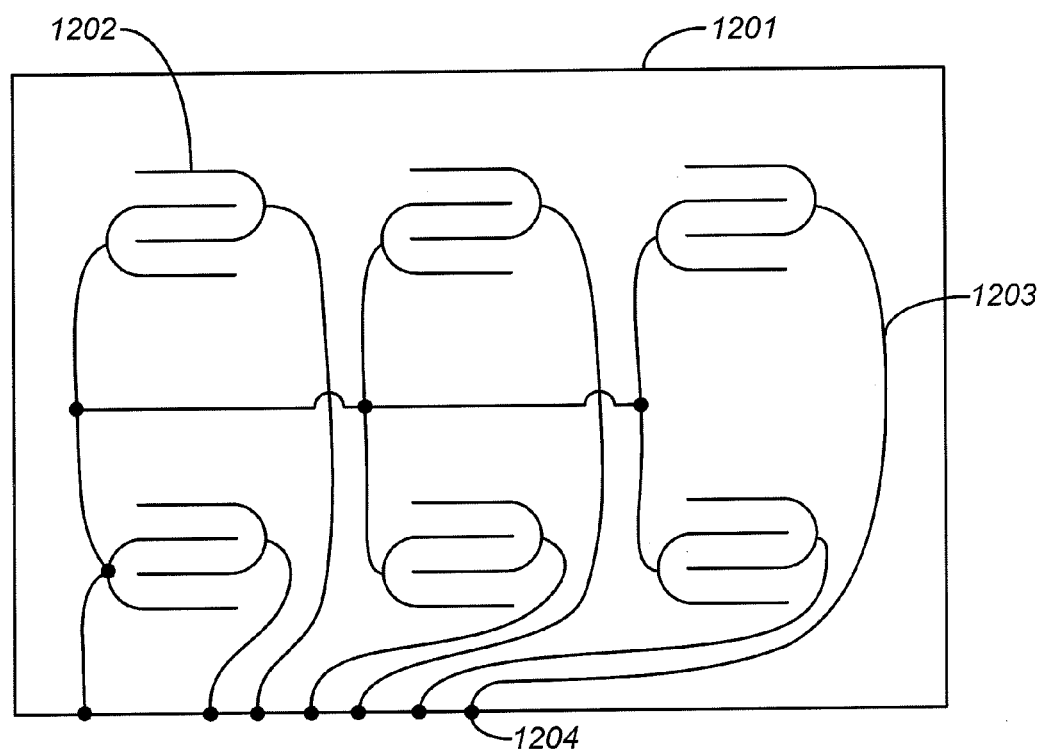
FIG. 12 is a diagram of the circuitry in the lid of the electroporator that includes the well plate of FIG. 10.

A further alternative for both the well plate and the lid are shown in FIGS. 10, 11, and 12. The well plate 1001 of which a top view is shown in FIG. 10 contains twelve wells 1002, although corresponding plates with 24, 96, or any other number of the same type of wells can be used. The wells in this plate are circular but, as in the embodiments described above, can be square, rectangular, or other shapes as well, and they can be cylinders extending upward from the plate surface or indentations in the body of the plate. The electrodes in these wells are a series of thin metal plates 1003 that, as shown in FIG. 11, extend a short distance above the outer perimeter of each well. Electrical contact with the plates is achieved along the protruding upper edges of the plates rather than at laterally extended contact areas adjacent to the rims of the wells. The upward protrusion of the plates facilitates this contact. As in the embodiment of FIGS. 7, 8, and 9, the plates do not extend to the floor 1004 of the well but instead terminate a short distance above the floor to provide clearance for cells at the bottom of the well. FIG. 12 depicts the lid 1201 and shows the traces 1202 in the form of rails that will contact the upwardly protruding edges of the electrode plates. The lid 1201 can be constructed as a printed circuit board on which the traces are plated by any of conventional plating processes known in the art. Various electrical leads 1203 in the lid joining the rails to connections 1204 at the edge of the lid are also shown.

In all of the embodiments shown above, the lids can be configured to fit securely over the well plate in a manner that will maintain the proper alignment of contacts between the lid and the plate, and that will prevent the lid from sliding. This can be achieved, for example, by incorporating a skirt around the lid periphery, or a groove to mate with a raised peripheral ridge on the plate, or any similar configuration. Other configurations will be readily apparent to those skilled in the art. The traces in the lid can be made in a modular format for insertion in the lid.

As a variation on the configuration shown in FIG. 11, the protruding upper edges of the thin metal plates 1003 can be replaced with tapered extensions such as trapezoidal extensions or sections terminating in a point, and the rails 1202 of FIG. 12 can be replaced by tulip contacts or similar resilient grasping contacts. Electrical connections will then be made by pressing the lid 1201 onto the well plate 1001.

While the foregoing description describes various alternatives to the components shown in the Figures, still further alternatives will be apparent to those who are skilled in the art and are within the scope of the invention.

What is claimed is:

1. An electroporator for electroporation of a plurality of samples, said electroporator comprising:
   a plate comprising a plurality of wells with upward-directed openings and with electrodes affixed inside said wells, said electrodes having extensions beyond said openings to provide contact areas;
   a lid with electrical circuitry terminating in exposed leads arranged to form electrical connections with said contact areas when said lid is closed over said plate; and
   a blank lid with no electrical circuitry, said blank lid and said lid with electrical circuitry being interchangeable.

2. An electroporator for electroporation of a plurality of samples, said electroporator comprising:
   a plate comprising a plurality of wells with upward-directed openings and with electrodes affixed inside said wells, said electrodes lining opposing sides of each of said wells and having extensions beyond said openings said extensions being horizontal contact areas with spacings between the contact areas of each pair of adjacent wells; and
   a lid with electrical circuitry terminating in exposed leads arranged to form electrical connections with said contact areas when said lid is closed over said plate.

3. The electroporator of claim 1 or 2 wherein said electrical circuitry is configured to energize said electrodes in groups of wells individually and in a predetermined sequence, each group constituting a fraction of said plurality of wells.

4. The electroporator of claim 1 or 2 wherein said electrical circuitry is configured to energize said electrodes in groups of wells, each group constituting a fraction of said plurality of wells, said electroporator further comprising programming means to energize each group of wells individually according to a protocol that varies among said groups by at least one parameter selected from the group consisting of waveform, voltage, capacitance, and resistance.

5. The electroporator of claim 2 wherein said electrodes are of narrower width along said upper edge than inside said well to prevent arcing between electrodes of adjacent wells.

6. The electroporator of claim 2 wherein said lid has an undersurface that is formed into downwardly opening shells with side walls and end walls, said side walls having edge surfaces complementary to said contact areas, said edge surfaces being of conductive material.

7. The electroporator of claim 6 wherein said end walls are shorter than said side walls.

8. An electroporator for electroporation of a plurality of samples, said electroporator comprising:
   a plate comprising a plurality of wells with upward-directed openings and with electrodes affixed inside said wells, wherein said electrodes are comprised of a plurality of baffles extending into the interior of each of said wells, with successive baffles in any single well defined as odd and even-numbered baffles, all odd-numbered baffles of each well joined to a common first horizontal platform extending outward from an upper edge of said well and all even-numbered baffles of each well joined to a common second horizontal platform extending outward from an upper edge of said well opposite said first horizontal platform; and
   a lid with electrical circuitry terminating in exposed leads arranged to form electrical connections with said first and second horizontal platforms when said lid is closed over said plate.

9. The electroporator of claim 8 wherein said wells have floors and said baffles have lower edges terminating above said floors.

10. The electroporator of claim 8 wherein said plate has an upper surface and said wells are cylinders extending upward from said upper surface.

11. An electroporator for electroporation of a plurality of samples, said electroporator comprising:
   a plate comprising a plurality of wells with upward-directed openings and with parallel plate electrodes mounted inside said wells, said electrodes having extensions that are portions of said plates extending vertically above said openings to provide contact areas; and
   a lid with electrical circuitry terminating in exposed leads arranged to form electrical connections with said contact areas when said lid is closed over said plate.

12. The electroporator of claim 11 comprising at least three of said electrodes per well.

13. The electroporator of claim 11 comprising four of said electrodes per well.

14. The electroporator of claim 11 wherein said exposed leads are rails equal in number and substantially equal in length to said extensions.

15. The electroporator of claim 11 wherein said wells have floors and said electrodes have lower edges terminating above said floors.

* * * * *